United States Patent [19]

Farina et al.

[11] Patent Number: 4,704,475

[45] Date of Patent: Nov. 3, 1987

[54] PREPARATION OF 3-HYDROXY-3-PHENYLBUTAN-2-ONE

[75] Inventors: James S. Farina, Swanton; Corbin L. Cummings, Isle LaMotte, both of Vt.

[73] Assignee: American Home Products Corporation (Del.), New York, N.Y.

[21] Appl. No.: 869,529

[22] Filed: Jun. 2, 1986

[51] Int. Cl.$^4$ .............................................. C07C 45/71
[52] U.S. Cl. ...................................................... 568/316
[58] Field of Search ........................ 568/316, 312, 715

[56] References Cited

U.S. PATENT DOCUMENTS 2,921,940  1/1960  Ramsden .............................. 568/715

OTHER PUBLICATIONS

Lapkin et al., J. Gen. Chem. U.S.S.R., vol. 19, pp. 669–675 (1949).
Kask et al., Chem. Abst., vol. 69, #35114a (1968).
Taulmets, Chem. Abst., vol. 82, #42803n (1975).
Trost et al., J. Org. Chem., vol. 45, pp. 2741–2746 (1980).
Lapkin and Golovkova, Zuhr. Obshchei Khim (J. Gen. Chem.) 19,701–6 (1949) Abstracted in Chemical Abstracts 44,1057h (1950).
Beilstein's Handbook (1969) at page 458.

Primary Examiner—James H. Reamer
Attorney, Agent, or Firm—John W. Routh

[57] ABSTRACT

A process is provided for preparing 3-hydroxy-3-phenyl-butan-2-one, useful in the preparation of acifran, in high yields by reacting 2,3-butanedione with the appropriate Grignard reagent at low temperature in tetrahydrofuran or admixtures thereof with toluene.

4 Claims, No Drawings

PREPARATION OF 3-HYDROXY-3-PHENYLBUTAN-2-ONE

BACKGROUND OF THE INVENTION (a) Field of the Invention

This invention relates to a process for the preparation of 3-hydroxy-3-phenylbutan-2-one by reaction of 2,3-butanedione with the appropriate Grignard reagent at low temperature and in the presence of tetrahydrofuran, or mixtures of tetrahydrofuran and toluene. More particularly, this invention relates to the preparation of 3-hydroxy-3-phenyl-butan-2-one by reaction of 2,3-butanedione with a Grignard reagent such as phenylmagnesium bromide at a temperature below about 10° C. in tetrahydrofuran, or mixtures of tetrahydrofuran and toluene.

(b) Prior Art

The preparation of 3-hydroxy-3-phenylbutan-2-one by reaction of 2,3-butanedione with an appropriate Grignard reagent is described in an article by Lapkin and Golovkova in Zuhr. Obshchei Khim (J. Gen. Chem.) 19, 701-6 (1949) and abstracted in Chemical Abstracts 44, 1057h (1950). The reaction of biacetyl with phenylmagnesium bromide (31.4 g) gave 30% methylphenylacetylcarbinol. The reaction conditions are not specifically described but earlier in the abstract the solvent used was diethyl ether and the reactants were heated for 10 hours. The preparation is also referred to in Beilsteins Handbook (1969) at page 458.

The use of 3-hydroxy-3-phenylbutan-2-one is described in U.S. Pat. Nos. 4,169,202 and 4,244,958 to make the compound 2-methyl-2-phenyl-3(2H)-furanone-5-carboxylic acid, known generically as acifran.

SUMMARY OF THE INVENTION

According to this invention a low temperature preparation in tetrahydrofuran or a mixture of tetrahydrofuran and up to 75% toluene is provided which gives high yields of relatively high purity 3-hydroxy-3-phenylbutan-2-one by reaction of the appropriate Grignard with 2,3-butanedione. The reaction advantageously is carried out at a temperature below about 10° C. with approximately equimolar proportions of reactants and at solution concentrations of about 20M to about 0.5M, the Grignard solution being added to the dione solution.

DETAILS OF THE INVENTION

Typical preparations of 3-hydroxy-3-phenylbutan-2-one are given in the examples below. Initially the reaction of 2,3-butanedione dissolved in tetrahydrofuran (23M) with commercial phenylmagnesium chloride dissolved in tetrahydrofuran (2M) was studied. Upon addition of 1 equivalent of the Grignard to the dione, the desired product was obtained in 42.9% yield after standard work-up. Short path distillation of the crude product, which NMR showed to contain aralkyl impurities, gave the desired product in 32.6% overall yield and 92.7% purity as determined by high pressure liquid chromatography.

Table I below shows the results of other runs conducted at temperatures ranging from −10° C. to +40° C. The yield was not significantly increased at +10° C. but declined by 50% when the reaction temperature was +40° C. with more aralkyl impurities as determined by NMR. Also, the addition of the dione to the Grignard reagent (Run 4, Table I) gave very little of the desired product. In all runs, the reaction was carried out under a nitrogen atmosphere. Crude product yields were estimated by NMR. The yields in parenthesis were after one distillation.

TABLE I

| Run | Temperature (°C.) | % Yield |
|-----|-------------------|---------|
| 1 | −10 | 42.9 (32.6) |
| 2 | 10 | 43.1 |
| 3 | 40 | 23.5 |
| 4 | −10 | — (15.7) |

Further improvements in yield of desired product were realized when more dilute solutions of 2,3-butanedione were employed. Addition of phenylmagnesium chloride (2M in THF) to a 2M THF solution of dione at −5° C.±4° C. gave crude product in 69.7% yield after work-up. The NMR spectrum of this material showed very little aralkyl impurity and gave, after one vacuum distillation, desired product of 94% strength (HPLC) in 60.4% overall yield. The crude yield of desired product was raised to 75.1% and 77% when 1M and 0.5M solutions of dione respectively, were employed.

The results are shown in Table II below. All reactions were carried out under nitrogen at −5° C.±4° C. with equimolar amounts of reagents and the Grignard added to the dione.

TABLE II

| Run | Dione Conc. in THF | % Yield |
|-----|--------------------|---------|
| 5 | 2 | 69.7 (60.4) |
| 6 | 1 | 75.1 (66.6) |
| 7 | 0.5 | 77.0 (69.3) |

Instead of using commercial phenylmagnesium chloride or phenylmagnesium bromide, the Grignard reagent can be generated in situ. Thus, phenylmagnesium bromide was generated in THF by adding bromobenzene to magnesium turnings in the presence of a catalytic amount of iodine. The resulting phenylmagnesium bromide solution (∼2M in THF) was added to an equimolar amount of 2,3-butanedione under optimal conditions (Run 6, Table II). After work-up, the desired product was isolated in 60.5% yield (Run 8, Table III), and contained only a trace, by NMR, of the aralkyl impurities previously observed. Short path vacuum distillation afforded 3-hydroxy-3-phenylbutan-2-one in 51.5% yield. Utilization of a 1.5M phenylmagnesium bromide solution, coupled with improvements in the technique for filtering and transferring the Grignard reagent to the dione, resulted in a 65.7% yield (56.5% distilled yield) of desired product (Run 9, Table III).

TABLE III

| Run | Equiv. PhMgBr | % Yield |
|-----|---------------|---------|
| 8 | 1 | 60.5 (51.5) |
| 9 | 1 | 65.7 (56.5) |

In Runs 8 and 9, the reactions were carried out under nitrogen at −3° C.±3° C. using 1M THF solution of 2,3-butanedione.

The process can also be run in mixtures of tetrahydrofuran and toluene, thereby making the process more economical. When 1.1 equivalent of phenylmagnesium bromide (1.9M in 50% THF/PhMe) was added to 2,3-butanedione in 50% THF/PhMe, crude product was isolated in 82.4% yield (Run 10, Table IV) after work-up. Short path vacuum distillation gave 3-hydroxy-3- phenylbutan-2-one in 68% yield. Alternatively, preparation of phenylmagnesium bromide in 38% THF/PhMe, followed by reaction with 2,3-butanedione in 38% THF/PhMe afforded 3-hydroxy-3-phenylbutan-2-one in 66.4% yield (Run 11, Table IV) after work-up and distillation. Similarly phenylmagnessium bromide in 25% THR/PheMe reacted with 2,3-butanedione in 25% THF/PheMe yielded 3-hydroxy-3-phenylbutan-2-one in 56.9% yield after work-up and distillation.

TABLE IV

| Run | Solvent | % Yield |
| --- | --- | --- |
| 10 | 50% THF/PhMe | 82.4 (68.0) |
| 11 | 38% THF/PhMe | — (66.4) |
| 12 | 25% THF/PhMe | 72.0 (56.9) |

In Runs 10 to 12, the reactions were carried out at $-5°$ C.$\pm 5°$ C. under nitrogen using 1M solutions of 2,3-butanedione. The yields after one distillation are given in parenthesis.

EXAMPLE I

The above laboratory scale runs provided data for a scale-up experiment which began by adding 47 ml of neat bromobenzene, dropwise, to 170.8 g of magnesium turnings and 0.1 g of iodine in 760 ml of THF at room temperature. Grignard reagent formation began immediately and the reaction rose to reflux. Next, 628 ml of bromobenzene dissolved in 1,480 ml of THF was added to the magnesium at such a rate as to maintain reflux. The reaction mixture was then stirred at reflux under nitrogen, diluted with 840 ml of THF, and cooled to approximately 35° C. Finally, the phenylmagnesium bromide solution ($\sim$1.5M) was transferred to an addition funnel via a filter candle in order to remove the unreacted magnesium.

While maintaining the temperature at $-4°$ C.$\pm 2°$ C., the Grignard reagent (6.39 moles) was added to 500 g (5.87 moles) of 2,3-butanedione dissolved in 5.29 L of THF. After a few hours the reaction was quenched with 5% sulfuric acid to a pH of 6-6.5 and extracted with toluene. The combined organic extracts were washed with 5% sodium bicarbonate, water, and concentrated in vacuo to give 604 g (50.9% yield) of crude product. Vacuum distillation (one time) of 300 g of crude product gave 194 g (.'.41% overall yield) of 3-hydroxy-3-phenylbutan-2-one as a yellow liquid.

EXAMPLE II

Charged 22.4 g of bromobenzene to 167 g of magnesium turnings in 630.6 ml of THF at room temperature. After Grignard reagent formation began (iodine crystals may be added to catalyze reaction), added 941 g of bromobenzene dissolved in 522.5 ml of THF and 1.94 L of toluene to the magnesium at such a rate as to maintain reflux. The resulting solution was then stirred at reflux 1 hour, cooled to less than 50° C., and transferred to an addition funnel.

The Grignard reagent (6.13 moles) was added to 480 g of 2,3-butanedione dissolved in 1.95 L of THF and 3.25 L of PhMe while maintaining the temperature at $-6°$ C.$\pm 4°$ C. After the reaction was complete, it was quenched with 5% sulfuric acid to pH=4.5$\pm$1, then worked up as in Example I to give 689 g of crude product. Vacuum distillation (88°-93° C., 1.2-3 mm Hg) gave 3-hydroxy-3-phenylbutan-2-one in 56.6% yield.

U.S. Pat. No. 4,244,958 in Example 3 illustrates a preparation of 3-hydroxy-3-phenyl-2-butanone using mercuric sulfate as a reactant. The process of this invention avoids the use of mercury compounds and employs readily available reagents. Example 4 of the said patent illustrates the production of acifran, a useful hypolipidemic agent in a mammal.

We claim:

1. In a process for the manufacture of 3-hydroxy-3-phenylbutan-2-one by reaction of 2,3-butanedione with a Grignard reagent, the improvement which comprises carrying out the reaction at a temperature below about 10° C. in tetrahydrofuran, or an admixture of tetrahydrofuran and toluene containing up to about 75% of toluene, in the presence of an inert gas, the Grignard reagent being added to the 2,3-butanedione.

2. The process of claim 1 wherein 1 to 1.2 equivalents of Grignard reagent are reacted with 2,3-butanedione.

3. The process of claim 2 wherein the Grignard reagent and the 2,3-butanedione are at solution concentrations of about 20M to about 0.5M.

4. In a process for the manufacture of 3-hydroxy-3-phenylbutan-2-one by reaction of 2,3-butanedione with a Grignard reagent, the improvement which comprises carrying out the reaction at a temperature below about 10° C. in an admixture of tetrahydrofuran and toluene containing about 25% to 75% by volume of toluene, in the presence of an inert gas, 1 to 1.2 equivalents of the Grignard reagent being added to the 2,3-butanedione and wherein the Grignard reagent and the 2,3-butanedione are at solution concentrations of about 2M to about 0.5M.

* * * * *